United States Patent [19]
Joseph et al.

[11] Patent Number: 6,015,045
[45] Date of Patent: *Jan. 18, 2000

[54] HYGIENIC PACKAGE WITH A RECLOSABLE FLAP

[75] Inventors: Gary Curtis Joseph; Charles John Berg, Jr., both of Cincinnati; Ricky Alan Pollard, Moscow, all of Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/695,281

[22] Filed: Aug. 9, 1996

[51] Int. Cl.⁷ ............................................. A61F 13/20
[52] U.S. Cl. ........................................ 206/494; 206/812
[58] Field of Search ................... 206/494, 804, 206/812, 823, 440, 438; 229/87.05, 87.01

[56] References Cited

U.S. PATENT DOCUMENTS

| | | |
|---|---|---|
| 3,021,002 | 2/1962 | Guyer . |
| 3,266,055 | 8/1966 | Graybill . |
| 3,970,215 | 7/1976 | McLaren et al. . |
| 4,420,080 | 12/1983 | Nakamura . |
| 4,458,810 | 7/1984 | Mahoney ............................ 206/210 |
| 4,460,088 | 7/1984 | Rugenstein et al. . |
| 4,468,811 | 8/1984 | Shaw et al. . |
| 4,540,091 | 9/1985 | Habock . |
| 4,709,399 | 11/1987 | Sanders . |
| 4,785,940 | 11/1988 | Wilson . |
| 4,786,190 | 11/1988 | Van Erden et al. . |
| 4,790,670 | 12/1988 | Barbaro . |
| 4,967,910 | 11/1990 | Schuster . |
| 4,979,613 | 12/1990 | McLaughlin et al. . |
| 5,018,625 | 5/1991 | Focke et al. . |
| 5,040,685 | 8/1991 | Focke et al. . |
| 5,121,879 | 6/1992 | Focke et al. . |
| 5,145,091 | 9/1992 | Meyers . |
| 5,165,545 | 11/1992 | Focke et al. . |
| 5,184,725 | 2/1993 | Reinheimer et al. . |
| 5,295,579 | 3/1994 | Focke et al. . |
| 5,333,735 | 8/1994 | Focke et al. . |
| 5,462,166 | 10/1995 | Minton et al. .................. 206/494 X |
| 5,505,296 | 4/1996 | Parker .......................... 206/494 X |
| 5,516,000 | 5/1996 | Freiburger et al. . |
| 5,524,759 | 6/1996 | Herzberg et al. . |

FOREIGN PATENT DOCUMENTS

| | | |
|---|---|---|
| 21 24 285 | 12/1971 | Germany . |
| 35 42 999 | 8/1986 | Germany . |
| 90 00 694 U | 6/1990 | Germany . |
| WO 94/08541 | 4/1994 | WIPO . |
| WO 96/11146 | 4/1996 | WIPO . |
| WO 96/11147 | 4/1996 | WIPO . |
| WO 96/36481 | 11/1996 | WIPO . |

OTHER PUBLICATIONS

Commercially Available Products: 1. Pro Natur Taschentucher, sold by Scott–Feldmuhle GmbH; 2. Softis 4 ply pocket tissues, sold by Zewa; and 3. Tempo 4 ply handkerchiefs, sold by VP–Schickedanz, a subsidiary of the present assignee. A sample of each product (3 total) is enclosed.

*Primary Examiner*—Jacob K. Ackun
*Attorney, Agent, or Firm*—Larry L. Huston; Donald E. Hasse; E. Kelly Linman

[57] ABSTRACT

A package for containing hygienic articles. The package has a dispensing aperture covered by a refastenably closable flap. The flap overlaps the dispensing aperture, to minimize external contamination. The aperture is made by a cut-out, leaving an opening in the material used to form the package. A separate retaining band is added to decrease the size of the opening so that the desired overlap can be maintained independent of the cut-out used to form the opening or the flap. The package is intact as presented to the user, and may completely enclose the hygienic articles after the first use of a hygienic article.

13 Claims, 4 Drawing Sheets

HYGIENIC PACKAGE WITH A RECLOSABLE FLAP

FIELD OF THE INVENTION

The present invention relates to packages for containing hygienic articles. More particularly the present invention relates to packages having a reclosable flap which protects the hygienic articles within the package from outside contamination.

BACKGROUND OF THE INVENTION

Hygienic articles are in constant use. Hygienic articles include those articles which are brought into intimate contact with the skin. If contaminated, hygienic articles expose the user to various risks, ranging from epidermal irritation to infection. Exemplary hygienic articles include facial tissue, wet wipes, bath tissue, adult and infant diapers, sanitary napkins, and cellulose pads as are commonly used for removal of makeup, etc.

Hygienic articles are often carried by the user in a purse, glove compartment, etc. To conveniently keep a convenient number of the hygienic articles together, a plurality of the hygienic articles are commonly grouped together in a single package. The package has an aperture through which the hygienic articles are dispensed, typically in serial, on an as-needed basis. After one hygienic article is removed from the package, the balance of the hygienic articles remain in the package for later use.

The packages are commonly made of an impervious film, typically a polyolefin. This film prevents external contamination from entering the package directly through the walls of the package.

The package frequently has a reclosable cover flap. The reclosable cover flap articulates between an open position and a closed position. The open position allows for dispensing hygienic articles from the package. In the closed position, the cover flap prevents the hygienic articles from inadvertently falling out of the package.

But the consumer expects more than a cover flap which merely prevents inadvertent loss of the hygienic articles within the package. The consumer expects a cover flap in the closed position to protect the hygienic articles from external contamination. Dust, etc., which enters the package and either visibly, or without cover flap in the closed position to protect the hygienic articles from external contamination. Dust, etc., which enters the package and either visibly, or without apparent visual indication, contaminates the hygienic articles and exposes the consumer to the aforementioned risks.

One attempt to deal with this problem has been to cut the aperture into the impervious film. The portion of the film complementary to the cut then forms the distal edge of the reclosable flap. The distal edge of the reclosable flap is then, by definition, a perfect match to the edge of the dispensing aperture. The flap is closed so that the two edges meet and are held in place, typically by a piece of tape which overlaps both the flap and the wall of the package adjacent the aperture. Prior to first use, the distal edge can be held in place by small frangible uncut lands, such as occur by perforations. The user breaks the lands or perforations, thus completing the cut upon first use.

This attempt has several drawbacks. First, the overlapping tape is very expensive. Overlapping tape can increase the cost of the reclosability feature of the package by at least 200 percent, compared to a printed adhesive which provides the same reclosure security.

Additionally, the edge of the flap and edge of the aperture almost never perfectly meet during reclosure, particularly after dispensing one or more of the hygienic articles. There is always some gap between these two edges. This gap allows contamination to enter. The gap occurs due to stresses caused by folding the flap over the package after one or more articles have been removed. Removal of the hygienic articles causes the flap and the package to shift in the direction normal to the flap and package mating surfaces, since the volume of the contents has been reduced. Furthermore, the user rarely meticulously aligns the flap with the cut opening during reclosure.

One approach to the misregistration of the edges is to cut the wrapper film in order to make the cover flap larger than the aperture to ensure consistent overlap upon reclosure. This arrangement requires that the shape of the distal edge of the cover flap match the shape of the complementary edge of the dispensing aperture. Rarely is one shape optimal for both edges. Furthermore, this arrangement requires the flap to be fully cut and separated from the package at the time of manufacture. However, it may be desired to leave the flap and package arrangement intact, but separated by lines of weakness having frangible lands. This arrangement keeps the contents secure until opened by the user.

It is an object of this invention to provide a package for hygienic articles which completely encloses the hygienic articles to reduce the risk of contamination, both before and after initial use by the consumer. It is further an object of this invention to provide such a package which allows for independently shaping the edges of the dispensing aperture and cover flap. Finally, it is an object of this invention to provide a package for hygienic articles which can be closed without the use and expense of an overlapping adhesive tape.

SUMMARY OF THE INVENTION

The invention comprises a package for containing hygienic articles. The package comprises a container body for holding the hygienic articles. The body has at least one wall with an opening therethrough. The opening is cut from the wall and has a first predetermined open area exposing a first exposed area of the hygienic articles. The package further comprises a retaining band juxtaposed with the opening and joined to the wall. The retaining band covers a portion of the exposed area thereby decreasing the first exposed area to form an aperture through which the hygienic articles are dispensed. The aperture has a second predetermined open area smaller than the first predetermined open area. A cover flap is hingedly connected to the container body. The cover flap is articulable from a first open position whereby the hygienic articles can be dispensed to a second closed position where the hygienic articles are not exposed outside the package. In the closed position the cover flap covers substantially all of the aperture. The package may further comprise a means to fasten the cover flap in the closed position.

For clarity, the trim, if any, is not shown in FIGS. 2, 3, 5 and 7.

DETAILED DESCRIPTION OF THE INVENTION

Figure 1:
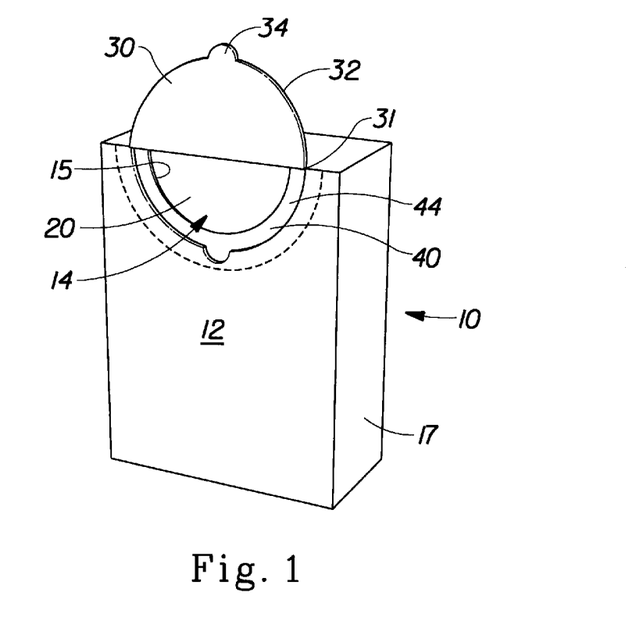
FIG. 1 is a perspective view of a package according to the present invention.

Referring to FIG. 1, the invention comprises a dispensing package 10. The dispensing package 10 may be generally parallelepipedly shaped as shown, or may be amorphous in shape. The dispensing package 10 has at least one wall 12 with an aperture 14 therethrough. The dispensing package 10 contains hygienic articles 20 which are dispensed by the user through the aperture 14. The aperture 14 is formed by the space between a retaining band 44 and a cover flap 30. When the cover flap 30 is articulated to an open position the aperture 14 can be located entirely within the wall 12 or extend from the wall 12 to other contiguous walls as desired.

Exemplary hygienic articles 20 include facial tissue, wet wipes, bath tissue, adult and infant diapers, sanitary napkins, and cotton or other cellulose pads as are commonly used for removal of makeup, etc. The sanitary napkins may be made according to commonly assigned U.S. Pat. No. 4,950,264, issued Aug. 21, 1990 to Osborn. The diapers may be made according to commonly assigned U.S. Pat. Nos. 3,860,003, issued Jan. 14, 1975 to Buell or 4,695,278, issued Sep. 22, 1987 to Lawson. The bath and facial tissues may be made according to commonly assigned U.S. Pat. Nos. 4,300,981, issued Nov. 17, 1981 to Carstens; 4,191,609, issued Mar. 4, 1980 to Trokhan or 4,637,859, issued Jan. 20, 1987 to Trokhan. Wet wipes may be made according to commonly assigned U.S. Pat. No. 5,332,118, issued Jul. 26, 1994 to Muckenfuhs. Make-up removal pads or other cleansing pads may be made according to U.S. Pat. No. 4,658,477, issued Apr. 21, 1987 to Caumont. The disclosure of each of the foregoing patents is incorporated herein by reference for the purpose of showing how to make exemplary hygienic articles 20 suitable for use with the claimed invention.

Examining the components of the dispensing package 10 in more detail, the dispensing package 10 may be made of any material 17 which can be formed to an outer wrapper to contain the hygienic articles 20. Preferably the material 17 is flexible, so that it can be folded to form the dispensing package 10 from a single sheet using an in-line operation. The material 17 is preferably impervious to prevent contamination through the dispensing package 10. Suitable materials 17 include polyolefinic films, foil, coated and uncoated papers, etc. It will be apparent that the dispensing package 10 may be provided with indicia, as desired.

The dispensing package 10 according to the present invention is preferably disposable, although it may be reusable. The dispensing package 10 is considered to be disposable if it is discarded after its contents are depleted and not restocked or replenished with hygienic articles 20. A dispensing package 10 is considered reusable if it is restocked with fresh hygienic articles 20 upon depletion.

If the dispensing package 10 is intended to be reusable and restocked with hygienic articles 20, the hygienic articles 20 may be compressed for shipment to the user. The hygienic articles 20 may be compressed according to the teachings of commonly assigned U.S. Pat. No. 5,507,130, issued Apr. 16, 1996 to Young et al., the disclosure of which is incorporated herein by reference.

Figure 2:
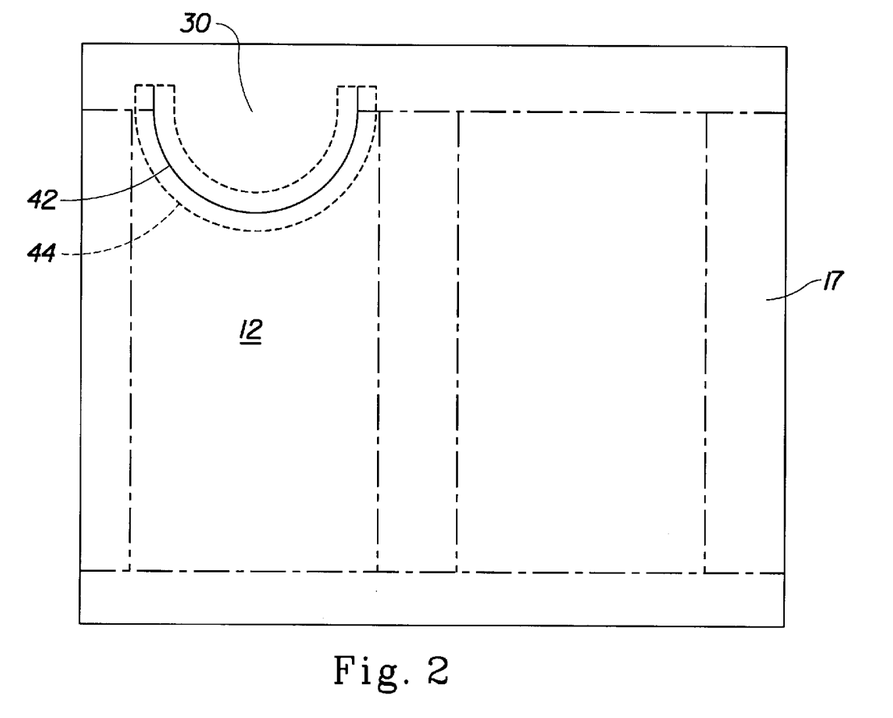
FIG. 2 is a top plan view of the material which can be utilized to make one package according to the present invention, having a vertical principal orientation, and showing the retaining band in phantom.
Figure 5:
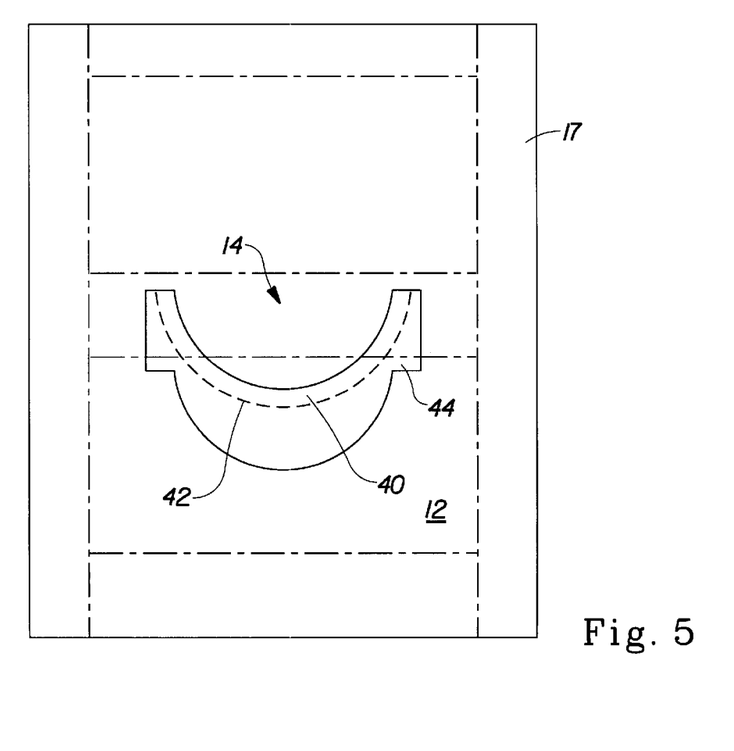
FIG. 5 is a top plan view of an alternative embodiment of the material which can be utilized to make one package according to the present invention, and showing the retaining band in phantom. The embodiment of FIG. 5 has a horizontal principal orientation and a tamper evident opening feature.

Referring to FIG. 2, the dispensing package 10 may be made according to the illustrated layout drawing. It is to be understood that FIGS. 2 and 5 represent the layout of two typical dispensing packages 10 in a continuous sheet of film type material 17 transported in the machine direction.

With continuing reference to FIG. 2, an opening 40 is made by cutting the material 17 in the continuous sheet or, alternatively, perforating the material 17 so that a cover flap 30 is formed at the point of first use. It will be apparent that the opening 40 may intercept two or more walls of the dispensing package 10 once the material 17 is folded to the desired shape. A portion of this material 17 later becomes the outer wrapper of one dispensing package 10 upon separation from the balance of the material 17 and folding. The opening 40 in the package made by the cutout has a first predetermined open area. The first predetermined open area is defined by the cut areas on the border formed by the fold line, or fold lines, which occur when the cover flap 30 is articulated to the open position. The predetermined open area of the opening 40 exposes a like first exposed area of the hygienic articles 20 inside the package.

The opening 40 may be cut into the individual packages 10 using a rotary die or a stamping die as are well known in the art. The shape of the opening 40 can be of any size and location on the dispensing package 10 as desired. The type of hygienic articles 20 to be dispensed, the number of hygienic articles 20 originally contained in the package 10, and the area of the hygienic articles 20 to be exposed for grasping and dispensing, as well as the required dispensing force, all influence the choice of the opening size and shape. Importantly, the cut which forms the opening 40 may be a continuous line, or, alternatively, may be a line of weakness in the material 17 which forms the outer wrapper of the dispensing package 10. If it is desired that the cut form a line of weakness, perforations 42 are suitable, or, alternatively, a cut which only partially penetrates the thickness of the material 17 may be utilized. The shape of the cut is preferably arcuate, as shown, and oriented concave towards the closest edge of the dispensing package 10. It will be apparent to one of ordinary skill that the shape of the cut determines the shape of the cover flap 30.

Figure 7:
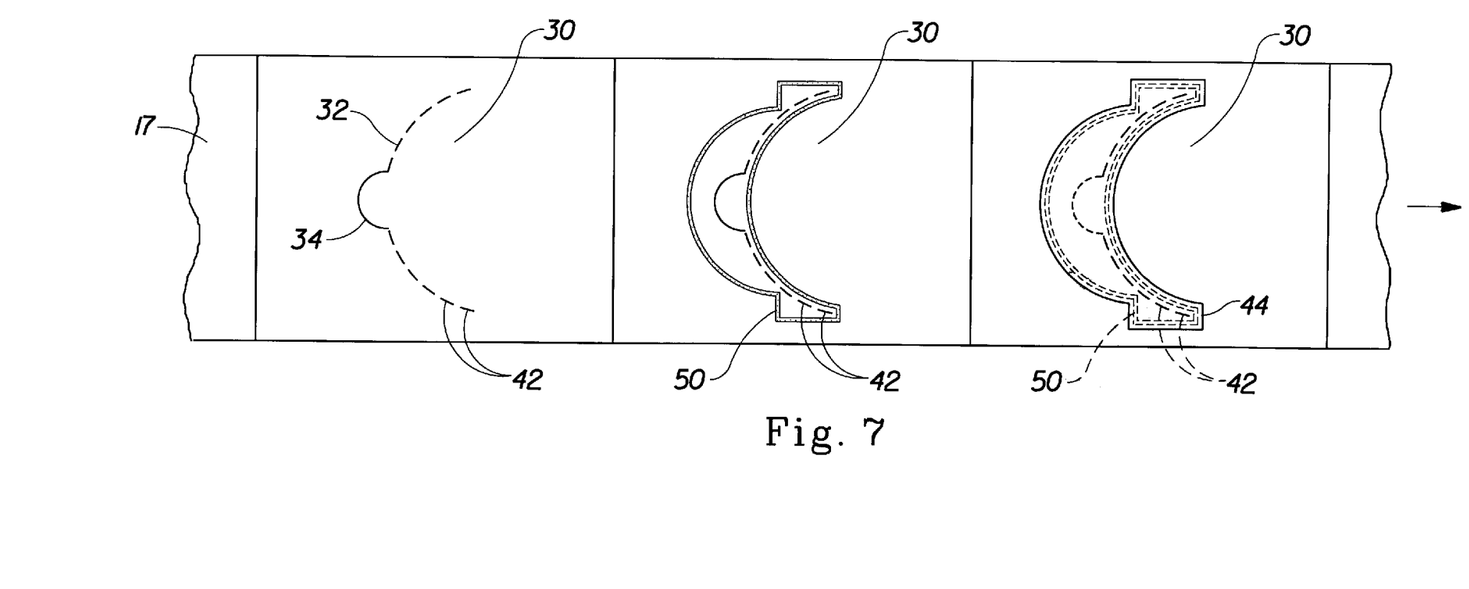
FIG. 7 is a fragmentary top plan view of a material which may be used to make the package according to the present invention, showing in succession, perforations, adhesive, and the retaining band being disposed on the material.

If the cut is a continuous line, as illustrated in FIG. 2, the dispensing package 10 will rely upon the fastening means to hold the cover flap 30 in the closed position, even prior to first use. Alternatively, if the cut comprises a line of weakness, as illustrated in FIG. 5, integrity of the outer wrapper of the dispensing package 10 will hold the hygienic articles 20 in place until first use. After the first hygienic article 20 is dispensed from the dispensing package 10, then the fastening means will hold the cover flap 30 in the closed position and thereby retain the hygienic articles 20 inside the dispensing package 10. Alternatively, a hybrid cut may be utilized as illustrated in FIG. 7. In FIG. 7 the cut comprises a continuous cut line forming the finger tab 34. This arrangement allows the user to easily grasp the finger tab 34 to open the cover flap 30 at the point of first use. However, the balance of the cut comprises a perforated line of weakness. The perforations 42 provide a tamper evident feature for security.

It is important to recognize the shape of the retaining band 44 will determine the shape of the final dispensing aperture 14. Preferably, the opening 40 intercepts two contiguous walls 12 for ease of dispensing.

With continuing reference to FIG. 7, another feature which can be incorporated into the package and influence the shape of the cover flap 30 is a finger tab 34. It is preferred the cover flap 30 have a finger tab 34. The finger tab 34 is any projection on or portion of the cover flap 30 easily grasped by the user and to which the user's attention is generally focused for opening the cover flap 30. The finger tab 34 may be centered on the cover flap 30 and particularly form the distal edge 32 of the cover flap 30. Generally the finger tab 34 is sized and shaped to be easily grasped by the thumb and forefinger and allows the force to be transmitted to the balance of the flap 30 so that it is articulated between positions. The finger tab 34 is preferably fully cut from the material 17 of the outer wrap and is therefore easily accessible by the user, even upon first use.

The finger tab 34 can be modified to have a greater thickness or a greater coefficient of friction to enable grasping. To increase its thickness, a second piece of film may be joined to the finger tab 34. Alternatively, the finger tab 34 thickness may be doubled by folding the film back on itself. Alternatively, the coefficient of friction of the finger tab 34 may be increased by printing or coating a resin, or a non-pressure sensitive adhesive onto the finger tab 34. Such modifications are applicable to either the inside, outside, or both surfaces of the finger tab 34.

A separate element can be affixed to the cover flap 30 to act as a finger tab 34. For example, a reclosable tape may serve this function, provided one recognizes the additional cost this will entail. The shape of the finger tab 34 and cover flap 30 can be designed to impart stress from the user as the flap is articulated to either the open or closed position. For example, a smooth, curvilinear transition in the distal edge 32 of the flap 30 along the finger tab 34 can minimize the risk of concentrating a large amount of stress at any point on the flap 30. This arrangement reduces the possibility of tearing or distorting the cover flap 30.

Referring back to FIG. 1, the material 17 may be folded into a suitable dispensing package 10, as illustrated by commonly assigned U.S. Pat. No. 5,184,725, issued Feb. 9, 1993 to Reinheimer et al., if a package having a hexahedronal shape is desired. Alternatively, the dispensing package 10 may be shaped as illustrated in commonly assigned U.S. Pat. No. 4,979,613, issued Dec. 25, 1990 to McLaughlin et al. The disclosures of both of the foregoing patents are incorporated herein by reference for the purpose of showing how to make dispensing packages 10 suitable for use with the present invention.

Figures 3, 4:
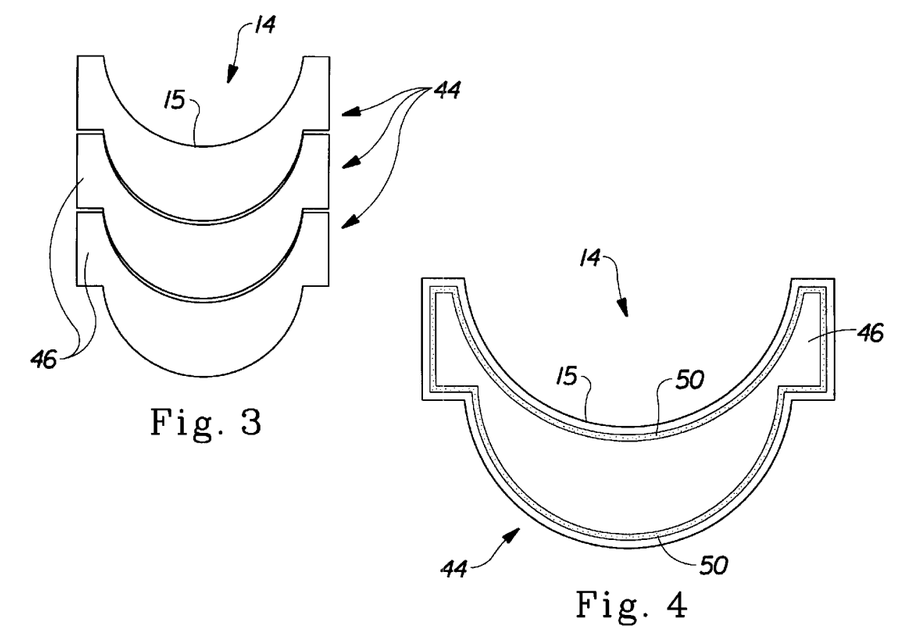
FIG. 3 is a top plan view of nested retaining bands which can be made according to the present invention.
FIG. 4 is a top plan view of an adhesive pattern for use with the retaining bands of FIG. 3.

Referring to FIG. 3, the retaining band 44 may be die cut from a continuous strip of material 17 on a slave line. The slave line may be separate from the line used to cut and form the material 17 which is later folded into the dispensing package 10. The retaining band 44 may, but preferably is not, shaped complementary to the edge of the dispensing opening 40. The retaining band 44 may have two flanges 46 at the outboard lateral extremities for attachment to the wall 12 of the dispensing package 10.

As described and claimed herein, the retaining band 44 is a separate component, joinable to the material 17 used to make the dispensing package 10. The retaining band 44 is preferably easily joined to the rest of the dispensing package 10. The retaining band 44 may be made of the same material 17 as is used to form the rest of the dispensing package 10, so that they are easily joined together for the intended life of the dispensing package 10. It may be desirable to use a less costly material for an internally disposed retaining band 44. For example, a thinner gauge material may be satisfactory, as the retaining band 44 need not provide for the integrity or puncture resistance of the package 10. Alternatively, the material used for the retaining band 44 may respond to the adhesive 50, whereas the package material 17 may not. The retaining band 44 may be joined to the balance of the package using adhesive 50, heat sealing, ultrasonic welding, or any other means as is well known in the art. Preferably any interior trim of the retaining band 44 is perforated, so that the consumer may remove it or so it will adhere to the backside of the cover flap 30 when articulated to the open position.

The wall 12 to which the retaining band 44 is joined has an inner surface, oriented towards the hygienic articles 20 and an outer surface opposed thereto and oriented away from the hygienic articles 20. The retaining band 44 is preferably joined to the inner surface of the wall 12, as noted above, although in a less preferred embodiment, the retaining band 44 may be joined to the outer surface of the wall 12. In an embodiment having the externally disposed retaining band 44, the first larger opening 40 and flap 30 will be cut into the external retaining band 44 and the overlap provided by a smaller opening cut into the film. The embodiment where the retaining band 44 is joined to the inner surface of the wall 12 is preferred because it allows one to use the same adhesive 50 to join the retaining band 44 to the dispensing package 12 as may be later optionally used to refastenably close the cover flap 30. The retaining band 44 need only overlap the wall 12 of the dispensing package 10 enough to ensure sufficient resistance to tear-out is present, so that the retaining band 44 does not become dislodged or inadvertently removed from the wall 12 during the intended life of the dispensing package 10. The retaining band 44 is juxtaposed with the opening 40 of the wall 12 and covers a portion of the opening 40, thereby decreasing the first predetermined area of the hygienic articles 20 which are exposed. By reducing the exposed area of the hygienic articles 20, the articles are more securely retained within the dispensing package 10, and a smaller area is presented for outside contamination.

This arrangement provides an aperture 14 through which the hygienic articles 20 may be dispensed. The aperture 14 has a second predetermined open area. The second predetermined open area is smaller than the first predetermined open area presented by the original opening 40 in the material 17.

The aperture 14 is preferably shaped and sized to permit convenient withdrawal of the hygienic articles. The aperture 14 may be symmetrical and curvilinear with an orientation concave towards the top of the dispensing package 10, as shown. The aperture 14 has an aperture edge 15. Preferably the aperture edge 15 is generally arcuately shaped as shown so that the hygienic articles 20 may be dispensed therethrough with only minimal risk of tearing or being caught by the distal edge of the aperture 14.

If desired, the dispensing aperture 14 may provide for both reach-in and pop-up type dispensing of the hygienic articles 20. Reach-in dispensing is preferred because the articles are more securely and hygienically contained in the dispensing package 10. Pop-up dispensing, while prophetically feasible, requires the cover flap 30 to overlay not only the retaining band 44 according to the present invention, but also any portion of the hygienic article 20 which extends outside the wall 12 of the dispensing package 10. A dispensing opening 40 providing for both reach-in and pop-up dispensing may be made according to commonly assigned U.S. Pat. No. 5,516,001, issued May 14, 1996 to Muckenfuhs et al, the disclosure of which is incorporated herein by reference.

Referring back to FIG. 1, the dispensing package 10 further comprises a cover flap 30. Preferably the cover flap 30 is integral with the material 17 used to form the outer wrap of the dispensing package 10, although, in a less preferred embodiment the cover flap 30 may be joined to the dispensing package 10 from a separate piece of material.

In either execution, the cover flap 30 is hingedly connected to the dispensing package 10. The cover flap 30 articulates from a first open position shown in FIG. 1 to a second closed position. In the open position the hygienic articles 20 may be dispensed through the aperture 14 as needed. Although it is generally understood the hygienic articles 20 will be dispensed in serial, if the aperture 14 is large enough relative to the size of the hygienic articles 20, multiple hygienic articles 20 may be concurrently dispensed.

The cover flap 30 is joined to the balance of the dispensing package 10 at and articulates about a proximal edge 31. The cover flap 30 further has a distal edge 32 which extends towards the retaining band 44 when the cover flap 30 is in the closed position and extends generally outward from the dispensing package 10 when the cover flap 30 is in the open position.

The cover flap 30 articulates to a second closed position wherein at least a portion of the cover flap 30 overlaps at least a portion of the retaining band 44. Preferably the overlap extends around the entire edge of the cover flap 30, particularly the distal edge 32 of the cover flap 30 and any finger tab 34. In the preferred arrangement, the overlap is preferably at least approximately two millimeters around the entire distal edge 32 of the cover flap 30, although the overlap will likely be greater at the finger tab 34.

The dispensing package 10 is further provided with a fastening means to fasten the cover flap 30 in the closed position. It will be understood by one of ordinary skill a second fastening means may be provided to temporarily fasten the cover flap 30 in the open position.

Suitable fastening means include hook and loop type fasteners, high static vinyl materials having attractive forces which form separable bonds, and preferably refastenable adhesive 50. Suitable hook and loop materials may be made according to commonly assigned U.S. Pat. Nos. 5,318,741, issued Jun. 7, 1994 to Thomas, or 5,116,563, issued May 26, 1992 to Thomas et al., both of which patents are incorporated herein by reference. High static vinyl closures may be made according to the aforementioned and previously incorporated commonly assigned '613 patent issued to McLaughlin et al.

Suitable refastenable adhesives include pressure sensitive adhesives which may be screen printed, sprayed, or otherwise conveniently applied in a predetermined pattern. A particularly suitable adhesive is available from the H. B. Fuller Company of Wauwautosa, Wis. under the designations HL-1459-X ZP and HL-2115-X. Adhesive coverage of 1.5 to 2.5 milligrams per square centimeter has been found suitable for the application described and claimed herein.

Referring to FIG. 4, the fastening means may be applied to the retaining band 44 or cover flap 30 as desired. Preferably, the fastening means is applied to the retaining band 44. This arrangement minimizes contamination of the fastening means by inadvertent contact with the hygienic article 20 being dispensed or the user's fingertips. Minimizing such contamination becomes increasingly important as a refastenable adhesive 50 fastening means is selected. The fastening means may be applied in a pattern which completely coats the retaining band 44 or, alternatively, may be congruent to the edges of the retaining band 44. For a typical adhesive 50 fastening means, a border of two to three millimeters between the adhesive 50 and the edge of the retaining band 44 has been found suitable. This arrangement provides for secure fastening of the cover flap 30 on the retaining band 44 in the closed position.

Referring to FIG. 5, the dispensing package 10 may have a horizontal principal orientation rather than a vertical principal orientation. This arrangement illustrates the flexibility of the present invention as applied to currently available machinery. The entire package design may be significantly altered with only minimal process changes. Only the width of the material 17 used to form the dispensing package 10, the width of the material used to form the retaining band 44, the pattern of the fastening means, and the die or other means used to cut the opening 40 and retaining bands 44 needs to be changed. Such flexibility is unattainable with early conventional manufacturing processes needed to produce the prior art dispensing packages.

Figure 6:
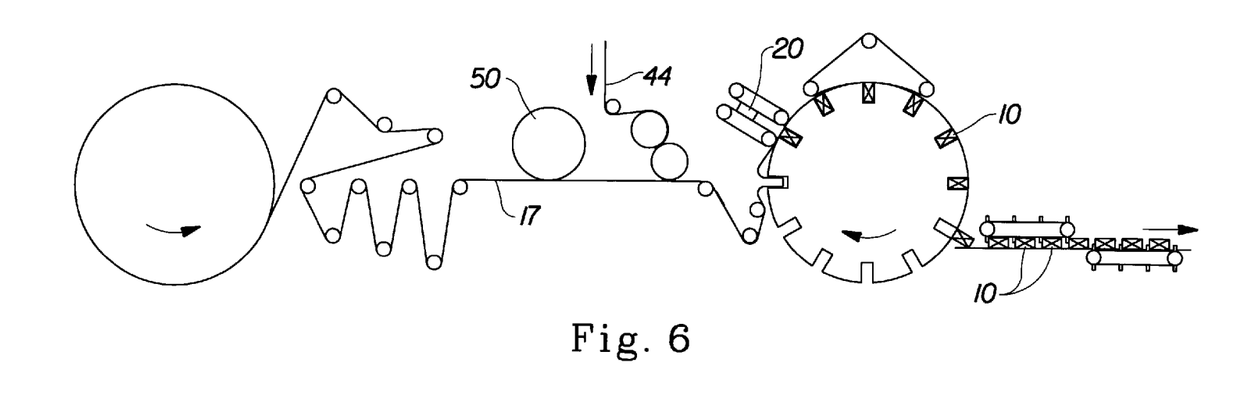
FIG. 6 is a schematic side elevational view of an apparatus which may be used to make the hygienic package according to the present invention.

Referring to FIG. 6, the dispensing package 10 may be produced as shown. The film, or other material 17, used to form the dispensing package 10 is be unwound from a conventional spool or other continuous supply. The adhesive 50 is screen printed, or otherwise disposed on the material 17 using known means such as spraying, gravure or flexographic printing, as desired. The retaining band 44 is then juxtaposed with the adhesive 50 and then joined to the film or other continuous material 17. The material 17 is then drawn into a receiving cavity on a turret by a vacuum or other suitable means. The hygienic articles 20 are inserted into the same cavity as the material 17 which forms the dispensing package 10 has been drawn into. The insertion of the hygienic articles 20 also serves to help inject the material 17 into the cavity. The continuous material 17 is cut to a discrete length. The cross machine edges of the outer wrapper of the dispensing package 10 are then folded using a conventional folding plow (not shown) or other means well known in the art and then heat sealed or joined with other known means such as adhesive or ultrasonic welding. The turret finally expels the dispensing packages 10 from the receiving cavity for folding and sealing of the ends using known means, such as folding plows and continuous band heat sealers.

FIG. 7 shows three stations of the material 17 used to form the dispensing package 10. At the first station the perforations 42 and the cut for the finger tab 34 are shown. It is to be recognized that the perforations 42 may be added to the material 17 by this station, or alternatively, may be pre-cut into the material 17 as received from the supplier.

At the second station the adhesive 50 is applied to the material 17, preferably by printing, although any of the other application means known and suitable may be utilized. Alternatively, the adhesive 50 may be applied to the outwardly oriented face of the retaining band 44. At the third station the retaining band 44 is applied to the material 17 and joined to what later becomes wall 12 of the dispensing package 10. The retaining band 44 is held in place by the adhesive 50. A pair of calender rolls (not shown) may be used to join the retaining band 44 to the material 17 of the outer wrapper of the dispensing package 10. At the next station (not shown) the material 17 is cut into discrete units for folding into the dispensing package 10.

It will be apparent that in the embodiment illustrated by the manufacturing process shown in FIG. 7, the dispensing package 10 is presented to the user with a cover flap 30 which completely encases the hygienic articles 20 prior to first use. When the user opens the dispensing package 10 the perforated seal is broken only at the point of first use. Importantly, the dispensing package 10 of the present invention still has a cover flap 30 which fully overlaps the retaining band 44 which is joined to the walls 12 so that the risk of contamination to the remaining hygienic articles 20 is minimized.

Furthermore, the shape of the retaining band 44 may be changed without altering the shape of the opening 40 cut from the material 17 and vice versa. By decoupling these shapes, maximum flexibility in the manufacturing process is obtained. Such flexibility is important if it is desired, for example, to sell different hygienic articles 20 in the same package. For example, it may be desired to make the finger tab 34 larger or smaller to accommodate different intended users.

Referring back to FIG. 5, in an alternative embodiment, the opening 40 is not entirely and continuously cut through the material 17. Instead, the opening 40 is perforated into the material 17. In this embodiment, when the consumer receives the package, the cover flap 30 is in the closed position. The cover flap 30 is torn from the material 17 to make the opening 40. When the cover flap 30 is articulated to the open position, the opening 40 is formed by tearing through the perforations 42 in the material 17. This arrangement provides a dispensing package 10 which is closed as presented to the consumer. If the perforations 42 are torn, this provides evidence the hygienic articles 20 inside of the package may have been subject to tampering. The cover flap 30 still overlaps the retaining band 44 so that upon reclosure the chances of external contamination are minimized.

Figure 8:
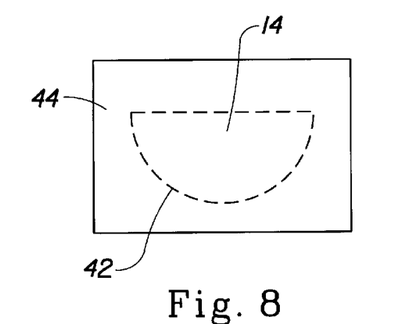
FIG. 8 is a top plan view of an alternative retaining band according to the present invention being rectangularly shaped and having a line of weakness forming a closed polygon.

Referring to FIG. 8, the retaining band 44 may be generally rectangularly shaped. This arrangement provides the advantage that the retaining band 44 is generally easier to handle during manufacture. However, this arrangement suffers from the disadvantage that more trim, and hence waste, is utilized One will note that in the embodiment of FIG. 8 that the perforations 42 form a closed polygon. This arrangement also provides the advantage that the dispensing package 10 is fully sealed as presented to the user.

The entirely rectangularly shaped retaining band 44 may be coated with adhesive 50. When the user opens the cover flap 30, the aperture 14 defined by perforations 42 is then torn from the balance of the dispensing package 10, allowing the hygienic articles 20 to be dispensed.

Figure 9:
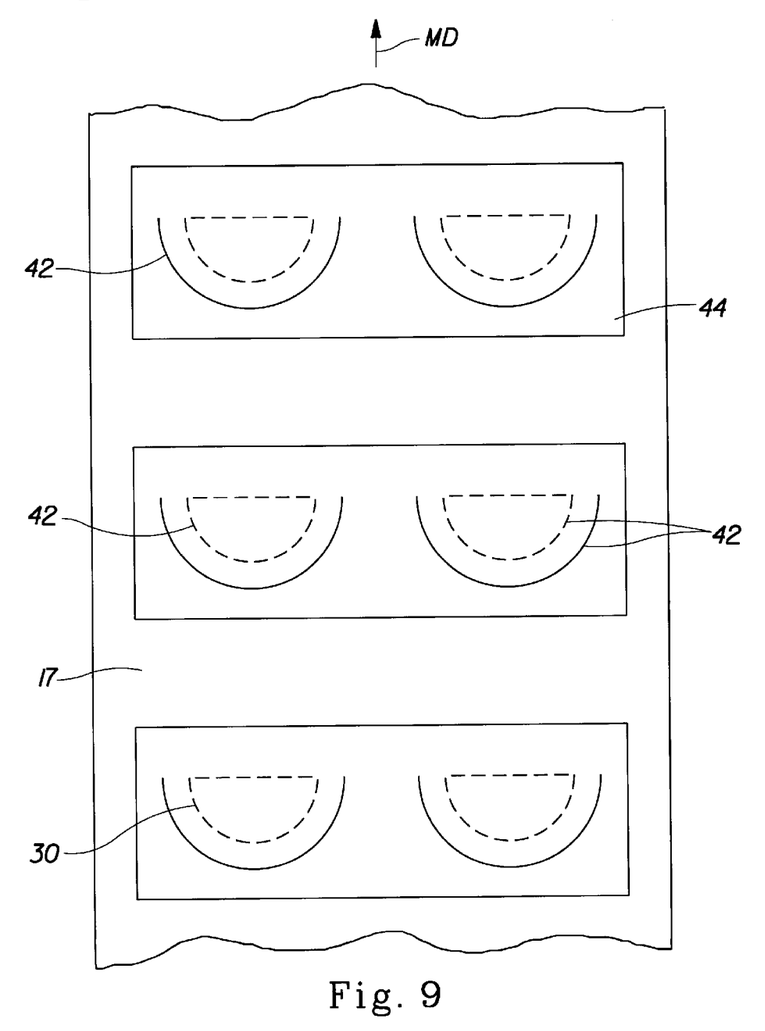
FIG. 9 is a fragmentary top plan view of a double width of the material according to the present invention having two rows of cuts and a single retaining band shown in phantom overlaying both rows of cuts.

Referring to FIG. 9, in manufacturing frequently two dispensing packages 10 are formed in side-by-side relationship. To accommodate conventional manufacturing equipment, the material 17 which forms the outer wrapper of the dispensing package 10 may be provided in a double width. The material 17 may have perforations 42 or cuts 42 as supplied. A single retaining band 44 overlays both side-by-side cuts 42 in the material 17.

The material 17 is transported in the machine direction indicated by the arrow MD. The material 17 may be longitudinally cut in half as desired. Each half of the material 17 which later forms a dispensing package 10 is then provided with an asymmetrically disposed retaining band 44 prior to being folded into the outer wrapper of the dispensing package 10. Although, if one were willing to incur additional cost, the retaining band 44 could be extended to the fill width of the material 17, resulting in a symmetric arrangement.

In other alternative embodiments, the dispensing package 10 may have two sets of dispensing apertures 14, each with its own cover flap 30. One aperture 14/cover flap 30 arrangement may be vertically oriented, the other horizontally oriented, etc. Additionally, the retaining band 44 interior trim, can be perforated and removed by the user to provide additional evidence of tampering or have indicia printed thereon. Further, one cover flap 30 can overlap two or more dispensing apertures 14.

Alternatively, the retaining band 44 interior trim may be adhered to the inside of the cover flap 30, so that when the cover flap 30 tears out, it removes this trim during initial opening, with the trim affixed to the interior side of the flap 30. The portion of the trim which is exposed to the user when the flap 30 is open may also be printed with indicia. Conventional tape can be used for the refastening means if one does not mind the added expense. Conventional tape which bridges the cover flap 30 and the wall 12 may be used in addition to the primary fastening means. If one desires to absolutely minimize expense, the refastening means may be omitted altogether in a less preferred embodiment.

What is claimed is:

1. A package for containing hygienic articles to be dispensed therefrom, said package comprising:

a container body for holding said hygienic articles, said container body having at least one wall with an opening therethrough, said opening being cut from said wall and having a first predetermined open area exposing a first exposed area of said hygienic articles;

a retaining band juxtaposed with said opening and joined to said wall, said retaining band covering a portion of said first exposed area, thereby decreasing said first exposed area to form an aperture through which said hygienic articles are dispensed, said aperture having a second predetermined open area smaller than said first predetermined open area;

a cover flap hingedly connected to said container body, said cover flap being articulable between a first open position whereby said hygienic articles can be dispensed and a second closed position whereby said hygienic articles are not exposed outside said package, whereby in said closed position said cover flap covers substantially all of said aperture; and a fastening means to fasten said cover flap in said closed position.

2. A package according to claim 1 wherein said cover flap has a proximal edge and a distal edge and said aperture has an aperture edge, said distal edge of said cover flap overlapping at least a portion of said aperture edge.

3. A package according to claim 2 wherein said wall has an inner surface and an outer surface, said retaining band being joined to said inner surface of said wall.

4. A package according to claim 3 wherein said retaining band has an aperture edge, wherein said aperture edge of said retaining band and said distal edge of said one flap are not complimentary.

5. A package according to claim 2 wherein said wall has an inner surface and an outer surface, said retaining band being joined to said outer surface of said wall.

6. A generally parallelepipedly shaped package for containing hygienic articles to be dispensed therefrom, said package comprising:

a generally parallelepipedly shaped container body for holding said hygienic articles, said container body having an opening therethrough, said opening intercepting at least two contiguous walls of said parallelepipedly shaped container body, said opening being cut from said walls and having a first predetermined open area exposing a first exposed area of said hygienic articles;

a retaining band juxtaposed with said opening and joined to at least one of said walls, said retaining band covering a portion of said first exposed area, thereby decreasing said first exposed area to form an aperture through which said hygienic articles are dispensed, said aperture having a second predetermined open area smaller than said first predetermined open area;

a cover flap hingedly connected to said container body, said cover flap being articulable between a first open position whereby said hygienic articles can be dispensed and a second closed position whereby said hygienic articles are not exposed outside the package, whereby in said closed position said cover flap covers substantially all of said aperture; and refastenable adhesive disposed on said retaining band to maintain said cover flap in said closed position.

7. A package according to claim 6 wherein said cover flap is integral with said container body.

8. A package for containing hygienic articles to be dispensed therefrom, said package comprising:

a container body for holding said hygienic articles;

a retaining band joined to said at least one wall, a line of weakness being disposed in said retaining band; and a cover flap connected to said body, said cover flap being articulable between a first open position and a second closed position whereby said hygienic articles are not exposed outside said package, said cover flap being joined to said retaining band at said line of weakness prior to dispensing a first said hygienic article through said aperture, said cover flap rupturing said line of weakness in said retaining band when said cover flap is articulated from said closed position to said open position, thereby forming an aperture upon first use, said hygienic articles being dispensable through said aperture when said cover flap is in said first open position, said cover flap overlapping and covering substantially all of said aperture when said cover flap is in said second closed position.

9. A package according to claim 8 wherein said cover flap has a proximal edge and a distal edge, and said aperture has an edge, wherein said distal edge of said cover flap is not complimentary to said edge of said aperture.

10. A package according to claim 9 wherein said cover flap is integral with and hingedly connected to said container body at said proximal edge.

11. A package according to claim 10 having a generally parallelepiped shape.

12. A package according to claim 9 wherein said package comprises a polyolefinic material.

13. A package according to claim 12 wherein said retaining band comprises a polyolefinic material.

* * * * *